United States Patent [19]

Abbatte et al.

[11] Patent Number: 5,055,039
[45] Date of Patent: Oct. 8, 1991

[54] ORTHODONTIC POSITIONER AND METHODS OF MAKING AND USING SAME

[75] Inventors: Gerard P. Abbatte, Buffalo; Peter R. Breads, Grand Island; Stephen P. Warunek, West Seneca; Brian D. Willison, Buffalo, all of N.Y.

[73] Assignee: Great Lakes Orthodontics, Ltd., Tonawanda, N.Y.

[21] Appl. No.: 254,216

[22] Filed: Oct. 6, 1988

[51] Int. Cl.⁵ ............................................. A61C 3/00
[52] U.S. Cl. ......................................... 433/24; 433/6
[58] Field of Search ...................... 433/6, 24; 128/861; 264/16

[56] References Cited

U.S. PATENT DOCUMENTS

| | | | |
|---|---|---|---|
| 2,531,222 | 11/1950 | Kesling | 128/861 |
| 3,738,005 | 6/1973 | Cohen et al. | 433/24 |
| 4,055,895 | 11/1977 | Huge | 128/861 |
| 4,551,096 | 11/1985 | Dellinger | 433/24 |
| 4,559,013 | 12/1985 | Amstutz et al. | 433/6 |
| 4,793,803 | 12/1988 | Martz | 433/6 |
| 4,856,991 | 8/1989 | Breads et al. | 433/6 |

Primary Examiner—Cary E. O'Connor
Attorney, Agent, or Firm—Hodgson, Russ Andrews, Woods & Goodyear

[57] ABSTRACT

An orthodontic positioner appliance of elastomer base material is formed directly on the tooth coupling members during fabrication so as to assure accuracy of the appliance and compliance with the exact shape and placement of the members. A construction model is provided of the patient's teeth in a desired orientation, members are attached to the teeth in the model, and the positioner is formed by applying material to the model and directly to the members providing an exact adaptation of the material to the model including the members and providing an exact fit between the material and the members so as to eliminate any void between the members and the material to assure maximum purchase on the teeth but yet be easily removed by the patient. A first form of the positioner is formed by a hand lay-up or other appropriate technique providing a positioner body in the form of strip of silicone elastomer material, the body having a surface facing the teeth and recesses in spaced relation along the strip for snap fitting onto the members, the positioner urging the patient's teeth to an exact fit between the recesses and the members so as to eliminate any void or space between the members and the recesses. A second form of the positioner is formed by molding providing an arcuate body of elastomer material including a trough for receiving teeth, the trough having walls with recesses in spaced relation for fitting onto the members.

30 Claims, 3 Drawing Sheets

ORTHODONTIC POSITIONER AND METHODS OF MAKING AND USING SAME

BACKGROUND OF THE INVENTION

This invention relates to the art of orthodontic appliances and methods, and more particularly to a new and improved orthodontic positioner and methods of making and using the same.

Elastic positioners in combination with attachments to the patient's teeth are employed in orthodontic treatments for achieving controlled tooth movement to a pre-determined position. In providing such appliances and treatments, it is important to move teeth to an ideal predetermined position with gentle controlled forces, maintain a more hygenic environment than that associated with conventional bracket/wire systems and to accomplish the foregoing in a manner acceptable to patients in both comfort and appearance. In addition, it has been found advantageous according to the present invention to fabricate the elastic positioner in a manner assuring accuracy of the appliance and complying with the exact shape and placement of the attachments or coupling members. This assures maximum purchase on the teeth but yet allows easy removal of the appliance by the patient. Furthermore, it has been determined beneficial according to the present invention to provide a positioner system and procedure which effectively results in substantially continuous application of forces to the patient's teeth in a manner acceptable to the patient and with the resulting advantage of relatively shorter overall length of treatment time.

SUMMARY OF THE INVENTION

It is, therefore, a primary object of the present invention to provide a new and improved orthodontic positioner appliance and methods of making and using the same.

It is a more particular object of this invention to provide such an appliance and method of making the same resulting in improved accuracy and compliance with the exact shape and placement of tooth attachments or coupling members.

It is a further object of this invention to provide such an appliance and method of making the same which assures maximum purchase of the appliance on the patient's teeth and yet allows easy removal therefrom.

It is a further object of this invention to provide such an appliance and method of using the same having enhanced patient acceptability in comfort and appearance.

It is a more particular object of this invention to provide such an appliance and method of using the same wherein the appliance and placement thereof on the patient's teeth are in two forms corresponding to portions of the day when the patient's mouth and teeth are most likely and least likely, respectively, to be visible to others.

It is a further object of this invention to provide such an appliance and method of using the same which effectively results in substantially continuous application of forces to the patient's teeth so as to reduce the overall length of treatment time.

It is a more particular object of this invention to provide such a method which is readily adaptable to placing attachments or coupling members on the patient's teeth both simultaneously and individually.

The present invention provides an orthodontic positioner appliance of elastomer base material which is formed directly on the actual tooth attachments or coupling members during the fabrication process so as to assure accuracy of the appliance and its compliance with the exact shape and placement of the attachments or coupling members. In the method of the present invention there is provided a construction model of the patient's teeth in a desired or ideal orientation, coupling members are attached to the facial and/or lingual surfaces of the teeth in the construction model, and the positioner is formed by applying positioner material to the construction model and directly to the coupling members thereby providing an exact adaptation of the positioner material to the construction model including the coupling members and providing an exact fit between the positioner material and the coupling members so as to eliminate any void or space between the coupling members and the positioner material to assure maximum purchase on the teeth but yet be easily removed by the patient. In a first aspect thereof, the positioner is formed by a hand lay-up or other appropriate technique in a manner providing a positioner body in the form of an elongated strip of silicone elastomer material having a length determined by the location of the coupling members and having a width initiating near the gingival line and terminating near the patient's opposing dental arch to avoid interference in occlusion, the body having a surface facing the teeth and recesses in spaced relation along the strip for snap fitting onto the coupling members, the positioner urging the patient's teeth to an exact fit between the recesses and the coupling members so as to eliminate any void or space between the coupling members and the recesses. In a second aspect thereof the positioner is formed by molding such as injection molding in a manner providing a positioner body of silicone elastomer material having an arcuate shape including a trough for receiving teeth of the dental arch, the trough having walls including surfaces having recesses in spaced relation along the trough for fitting onto the coupling members, the positioner urging the patient's teeth to an exact fit between the recesses and the coupling members so as to eliminate any void or space between the coupling members and the recesses to assure maximum purchase on the teeth but yet be easily removed by the patient. In a method of orthodontic treatment according to the present invention, coupling members are attached to the surfaces of the patient's teeth in a predetermined manner, only the first positioner is installed on the patient's teeth during a portion of the day when the teeth are most likely to be visible to others, and only the second positioner is installed on the patient's teeth during the remaining portion of the day when the teeth are least likely to be visible to others. The coupling members are attached to the patient's teeth using a transfer matrix formed from the construction model with coupling members attached thereto.

The foregoing and additional advantages and characterizing features of the present invention will become clearly apparent upon a reading of the ensuing detailed description together with the including drawing wherein:

BRIEF DESCRIPTION OF THE DRAWING FIGURES

DETAILED DESCRIPTION OF THE ILLUSTRATED EMBODIMENTS

Figure 1:
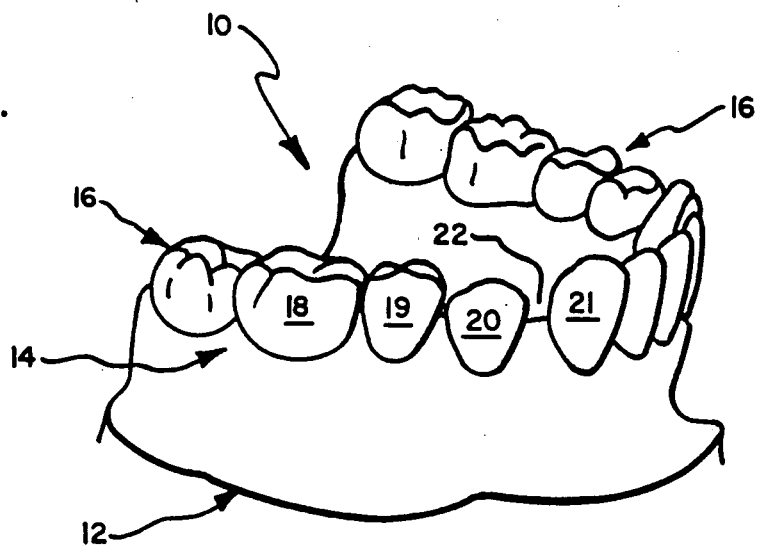
FIG. 1 is a perspective view of an original model of a patient's dental arch wherein the teeth therein are positioned in the actual and maloccluded orientation.

In previous orthodontic positioners, elastic forces are applied to the teeth in order to draw teeth to a predetermined position. To accomplish the goal of achieving controlled tooth movement to a predetermined position, in the method of the present invention the model teeth are repositioned in wax, utilizing accepted standards of occulsion or special instructions provided by the dentist as a guide. This will allow the practitioner to react to the accepted standards of occlusion and individualize tooth movement based on personal preferences. In order to control tooth movement, it is necessary to establish an attachment or a purchase to the teeth, so that the elastic appliance will snap on to the teeth gently drawing them to the predetermined position of the wax setup. In order to accomplish this, the present invention utilizes mushroom shaped lingual buttons which produce a snap on effect to the teeth. To assure the accuracy of the appliance and to comply with the exact shape and placement of the buttons, in accordance with the present invention, the elastic appliances are fabricated directly to an actual lingual button which is placed on either the lingual or facial surface, not an impression of the button. Because of the ability of the elastomeric material to snap on to the button that is attached to the tooth, the elastic material needs to be very flexible with excellent rebound and gentle forces. Thus, the elastomer used according to the present invention has been selected to be a silicone with two different durometers, about 40 for extensive movement and about 65 for finishing. The main appliance encompasses both lower and upper arches and is referred to as the nighttime appliance. Additionally, a daytime appliance is formed with a strip of elastomer attached to the buttons and extending as desired or prescribed, for example from molar to molar on the facial surface. This daytime appliance is fabricated to the ideal setup and is attached to the individual buttons and teeth; thus, it applies forces to the teeth and additionally eliminates any irritation that may occur by the buttons rubbing on the mucosa (inner lips and cheeks).

The objective with these appliances (daytime and nighttime) according to the present invention is to move teeth to an ideal predetermined position with gentle controlled forces, maintaining a more hygenic environment than conventional bracket/wire systems and being more acceptable to patients.

Because identical attachments are being placed to the duplicate of the wax setup for fabrication of the appliances there is need to construct a transfer matrix that will transfer the position of the buttons from the ideally repositioned teeth to the malaligned teeth and then to the patient. This is accomplished by using silicone impression putty to form a transfer tray. The transfer tray is then sectioned to individual teeth, buttons are inserted into the sockets, and then the buttons placed on each tooth of the malaligned original models. To form a full arch transfer matrix, the individualized sections are placed on each tooth of the malaligned arches and a thin overlay of thermoplastic material is formed over the sections to form a matrix to transfer the buttons to the patient. The transfer matrix can be cut into two or three parts by the practitioner for ease of applying buttons to the patient's teeth.

Figure 2:
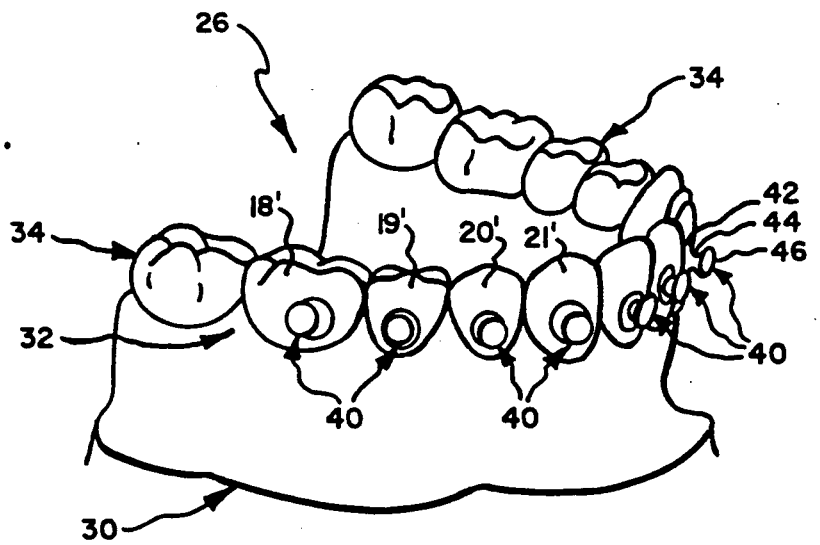
FIG. 2 is a perspective view of a construction model of the patient's dental arch shown in the model of FIG. 1 but wherein the teeth are positioned in a desired orientation and wherein coupling members are attached to the surfaces of the teeth in accordance with the method of the present invention.

Referring now to FIGS. 1 and 2, in the method of the present invention there is provided a construction model of the patient's teeth and a portion of the gum tissue in the dental arch wherein the teeth therein are positioned in a desired orientation. The construction model is formed in the following manner. Initially impressions are taken in the patient's mouth of the teeth located in the upper and lower dental arches, and die stone models, also designated original models, are formed from these impressions. The foregoing technique is well known in the art so that a detailed description thereof is believed to be unnecessary. Briefly, by way of example, according to the alginate impression technique, an amount of uncured alginate composition is introduced into an impression tray which then is inserted in the patient's mouth with the alginate composition appropriately seated onto the teeth. The uncured alginate composition being relatively liquid, flows around the teeth to effectively capture the detail of the shape and contour of the teeth. The alginate composition then is allowed to set whereupon the impression is removed from the mouth. The foregoing technique is given by way of example, and other known impression techniques can be employed.

Thereafter, a die stone composition in an uncured condition is provided and placed in the impression to form a hard die stone facsimile of the patient's dental arch and adjacent mouth structure which subsequently and in a hardened condition is removed from the impression. The nature of the die stone composition and method of making the die stone facsimile are well known to those skilled in the art so that the detailed description is believed to be unnecessary. Two die stone models are formed, one serving as the original model for use in the method and the other serving as a reference. Thus, an original model of a patient's dental arch, for example the lower arch, is designated 10 in FIG. 1 and includes a base 12, gum-tissue simulating portion 14 and teeth simulating portion 16. In the illustrative model 10, the teeth elements designated 18, 19, 20 and 21 are maloccluded with an undesired space 22 located between 20 and 21. In order to correct the malocclusion and reduce or eliminate space 22 by virtue of the orthodontic treatment, the patient's teeth represented by elements 18, 19 and 20 are to be rotated slightly clockwise about the respective axes of rotation and the tooth represented by element 21 is to be rotated slightly counterclockwise about its axis of rotation. By way of background, a more detailed description of taking impressions from the patient's mouth and of making die stone original models may be found in pending U.S. patent application Ser. No. 46,087 filed May 5, 1987, now U.S. Pat. No. 4,856,991 entitled "Orthodontic Finishing Positioner and Method Of Construction" and assigned to the assignee of the present invention.

The original model 10 of FIG. 1 is used to form a construction model, designated 26 in FIG. 2, in the following manner. Original models of the patient's upper and lower dental arches are mounted in a dental articulator by means of a face-bow transfer technique. In particular, the upper and lower original die stone models are operatively positioned within a dental articulator. To ensure the proper index or bite relationship between the models, adjustments are made to the articulator in accordance with a recorded centric relation or repositioning wax bite and a maxillary cast obtained from the patient's orthodontist and in accordance with standard face bow techniques. The method of obtaining wax bites and maxillary casts from the patient and subsequently utilizing the same to operatively position the models in an articulator are well known to those skilled in the art so that a detailed description thereof is believed to be unnecessary.

The next step in forming the construction model is repositioning the teeth of the original model to a desired or ideal position or orientation. In particular, the tooth simulating elements of each original model in the articulator which are to be repositioned are each separately cut or sawed from the remainder of the model. In the exemplary or original model of FIG. 1, tooth elements 18, 19, 20 and 21 will be separated from model 10. The tooth simulating elements are each cut from the remainder of the model in the dental interproximal area thereof and shaped in the root area thereof so that each tooth-simulating element has a V-shaped or wedge-like base. Once each tooth element is cut and removed from the model, the base of the tooth element can be further shaped using a cutting device on a lathe. Next, wax which has been warmed to a flowable condition is placed in the region of the model from which the tooth element is removed, the tooth elements are repositioned in this original location on the model with the bases thereof held in the wax so that once the wax is cooled the teeth elements are secured therein. The wax upon setting simulates the gum tissue area in the region of the bases of the teeth elements.

Finally, the particular ones of the teeth elements in either or both models which are held in wax are reset to a desired or ideal orientation in accordance with a predetermined or prescribed arrangement. In particular, the portion of the wax which surrounds a tooth simulating element desired to be moved is softened, such as by brush-flaming the wax with an alcohol torch, and then the tooth element is manually moved to a desired orientation and carefully released to avoid any shifting or movement from that orientation. Each tooth simulating element which is to be repositioned to a desired orientation is moved individually in the foregoing manner. In accordance with a preferred mode of the present invention, the repositioning of the teeth elements in wax utilizes the zero-based occlusion as a guide. Zero-based occlusion is one form of repositioning guide based upon accepted standards which are well-known to those skilled in the art so that a detailed description is believed to be unnecessary. This is believed to allow orthodontist to react to zero-based occlusion and individualized tooth movements based on their personal preferences. After repositioning of the teeth elements is completed, the gum simulating portion of each model can be built up and smoothed with wax as necessary to provide the models with the appearance of a healthy gum anatomy.

A positioner construction bite is taken by opening the articulator to move the proposed model surfaces about 7 millimeters apart and locking the incisal pin of the articulator. Next, a thin sheet of wax is inserted between the occlusal arches and the articulator is closed to the incisal pin setting. The construction bite registers an opening or space between the upper and lower arches sufficient to accommodate the thickness of one form of appliance and to allow for breathing holes in a full positioner appliance which will be described in detail presently. The foregoing techniques of repositioning the model teeth elements in wax are well known to those skilled in the art so that a detailed description thereof is believed to be unnecessary. By way of background, a more detailed description thereof may be found in pending U.S. patent application Ser. No. 046,087 filed May 5, 1987 entitled "Orthodontic Finishing Positioner And Method Of Construction" and assigned to the assignee of the present invention, the disclosure of which is hereby incorporated by reference.

The wax-stone models from the articulator, with the particular teeth elements repositioned to the ideal or desired orientation, then are duplicated using an appropriate impression technique, such as the alginate impression technique previously described. Then a die stone model is formed using this impression which is the construction model designated 26 in FIG. 2 wherein the teeth simulating elements are positioned in the desired or ideal orientation. In particular, model 26 has a base 30, gum tissue simulating portion 32 and teeth simulating portion 34. In the illustrative model, the repositioned tooth elements are designated 18', 19', 20' and 21' which teeth elements are in the desired or ideal orientation.

The next step in the method of the present invention is attaching coupling members to the facial and/or lingual surfaces of the teeth in the construction model. As shown in FIG. 2, according to a preferred mode of the present invention, each of the coupling members generally designated 40 includes an undercut and is in the illustrative form of a mushroom shaped lingual button formed of plastic and having a color so as to blend visually with the patient's teeth. In particular, each coupling member includes a generally circular base 42, a stem portion 44 of relatively smaller diameter extending from base 42 and a bulbous outer portion 46 at the end of stem 44 and spaced from the surface of the tooth to which the coupling members are attached. Stem 44 is generally cylindrical in shape and base 42 has a generally convex outer surface and a slightly concave opposite or end surface for conforming to the surface of the tooth to which it is attached. Depending upon the types of teeth to which the coupling member is attached, i.e. front teeth vs. molars, the base surfaces can have different degrees of concavity. The coupling members 40 are glued to the corresponding teeth using a suitable adhesive, for example fast set cyanoacrylate type. Each coupling member has a longitudinal axis, and according to a preferred mode of the present invention each coupling member is positioned on the tooth with the longitudinal axis of the coupling member in substantial alignment or registry with the center of rotation or axis of rotation of the tooth. In particular, satisfactory results have been obtained when the longitudinal axis of the coupling member is located about one third the distance between the gum line and the occulsal edge of the tooth and centrally of or midway between the vertical side edges of the tooth. The number of teeth to which individual coupling members 40 are attached is determined by the number of teeth to be repositioned, and in the illustration of FIG. 2 the coupling members 40 extend from the first molar on one side of the dental arch to the first molar on the opposite side. Furthermore, although the coupling members 40 are attached to the facial surfaces of the teeth in the illustration of FIG. 2, coupling members also can be attached to the lingual surfaces of the teeth depending upon the nature of the orthodontic treatment.

The foregoing illustrative coupling members 40 are commercially available from Rocky Mountain Orthodontics under the designation Plastic Lingual Buttons A-3901. Other forms of coupling members, attachments or brackets can be employed which include an undercut feature to provide a snap on effect.

Figure 3:
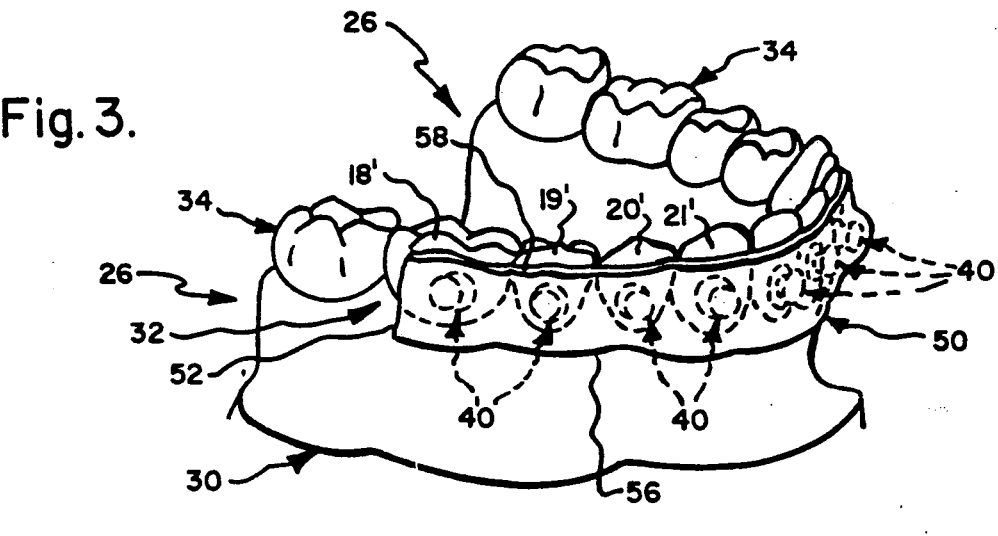
FIG. 3 is a fragmentary enlarged perspective view of the construction model FIG. 2 illustrating a positioner formed thereon in accordance with one aspect of the present invention.

In accordance with the present invention, a positioner is formed by applying positioner material to the construction model 26 and directly to the coupling members 40 thereby providing an exact adaptation of the positioner material to the construction model including the coupling members and providing an exact fit between the positioner material and the coupling members so as to eliminate the void or space between the coupling members and the positioner material. Thus, positioner material is applied directly to the actual coupling members or attachments 40, not to impressions thereof. FIG. 3 illustrates one form of positioner 50 according to the present invention. The positioner 50 illustrated in FIG. 3 is formed by performing a hand layup technique in a manner providing a positioner body in the form of an elongated strip having a length determined by the location of the coupling members or the number of teeth to be positioned and having a width initiating near the gingival line and terminating near the patient's opposing dental arch to avoid interference in occlusion, i.e. commensurate with the distance between the gum line and the occlusal/incisal edges of the teeth. In particular, there is provided a strip from a sheet of uncured hand lay-up form of silicone elastomer material. The length of the strip between the ends, one being designated 52, is determined by the number of teeth to be repositioned or by the location of the coupling members. The width of the strip ideally is selected such that the lower edge 56 is about one millimeter spaced from the patient's gum line and the upper edge 58 is spaced about 2 millimeters from the occlusal edge of the patient's teeth. The strip then is pressed using one's fingers onto the model 26 and coupling members 40, in particular into contact with the surfaces of the tooth elements and embedding the coupling members 40 as shown in FIG. 3. While a hand lay-up technique has been described by way of example, positioner 50 alternatively can be formed by injection or compression molding or other suitable techniques which would not dislodge or destroy coupling members 40.

After the positioner 50 is so formed by the hand layup techniques the material is further formed and then cured, preferably by application of heat and pressure. In particular, construction model 26 bearing attachments 40 with positioner 50 formed thereon is placed in a dental molding machine of the type marketed by Great Lakes Orthodontics Ltd., Buffalo, N.Y. under the designation Biostar. For a more detailed description of such a machine and its method of operation reference may be made to U.S. Pat. No. 3,768,164 issued Oct. 30, 1973 and entitled "Method Of Making A Dental Appliance", the disclosure of which is hereby incorporated by reference. The model 26 and positioner strip 50 can be covered with a thin sheet of rubber of the type commercially available from Hygenic Corp. under the designation Dental Dam. The dental molding machine then is closed and operated to apply pressure which enhances the forming and adapting of the positioner strip 50 to the attachments 40 and model surfaces. Then the model 26 with positioner strip 50 thereon is removed from the machine and placed in an oven for curing at a temperature determined by the nature of the material and so as not to damage the coupling members 40. By way of example, in an illustrative method and apparatus, the material of strip 50 is a hand lay-up form of Silastic medical-grade elastomer commercially available from Dow Corning Corporation under the designation MDX-4-4515 or MDX-4-4516. For this illustrative material, the curing time and temperature are 90 minutes at 250° F. Other forms of low durometer, high elasticity elastomers can be employed.

After curing, strip 50 is removed from model 26 simply by peeling it off from the model 26 and the coupling members 40. The strip then is trimmed to compensate for any variations in the desired dimensions for purposes of comfort, fit and appearance. While strip 50 is illustrated for use on the facial surfaces of the teeth, it could be formed for use on the labial surfaces. The manner of using positioner 50, both alone and in conjunction with other forms of positioners, and the advantages arising therefrom will be described in detail further on in the specification.

In order to install positioner 50 on the patient's dental arch or to install other forms of the positioner according to the present invention which will be described, it is necessary to attach coupling members to the patient's teeth. According to the present invention, coupling members identical to those designated 40 in FIGS. 2 and 3 are attached to the sides of the patient's teeth in accordance with the locations of coupling members 40 attached to the teeth elements of construction model 26. Because in the method of the present invention as previously described attachments are placed on construction model 26 for fabrication of the appliance, it is necessary to transfer the position of each attachment or coupling member from the ideally repositioned tooth of construction model 26 to the malaligned teeth represented in original model 10 and then to the patient's teeth. In accordance with the present invention, a transfer matrix is formed from construction model 26 with coupling members 40 attached to model 26 for use in attaching identical but separate coupling members to the patient's teeth. The transfer matrix is formed according to the present invention in the following manner.

Figure 4:
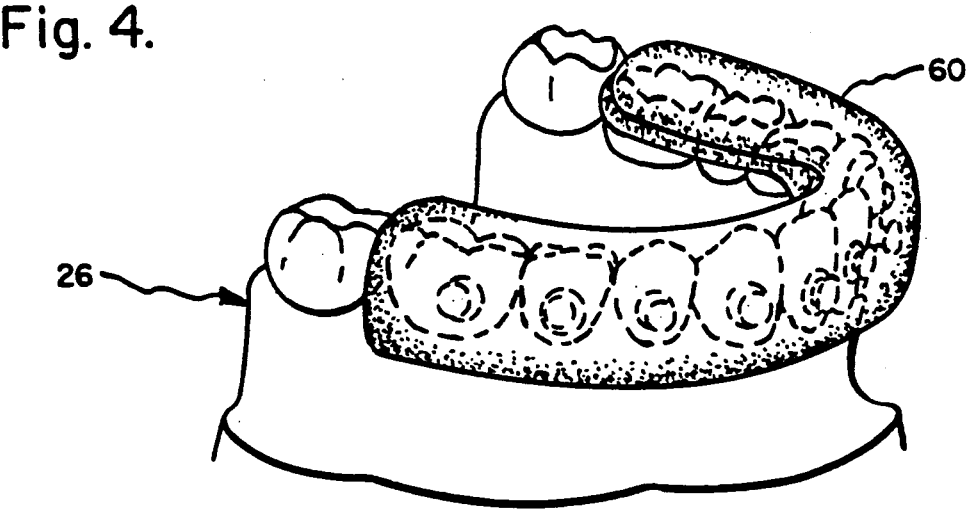
FIG. 4 is a fragmentary perspective view of the construction model of FIGS. 2 and 3 and illustrating one stage in the method of forming a transfer matrix according to the present invention.
Figure 5:
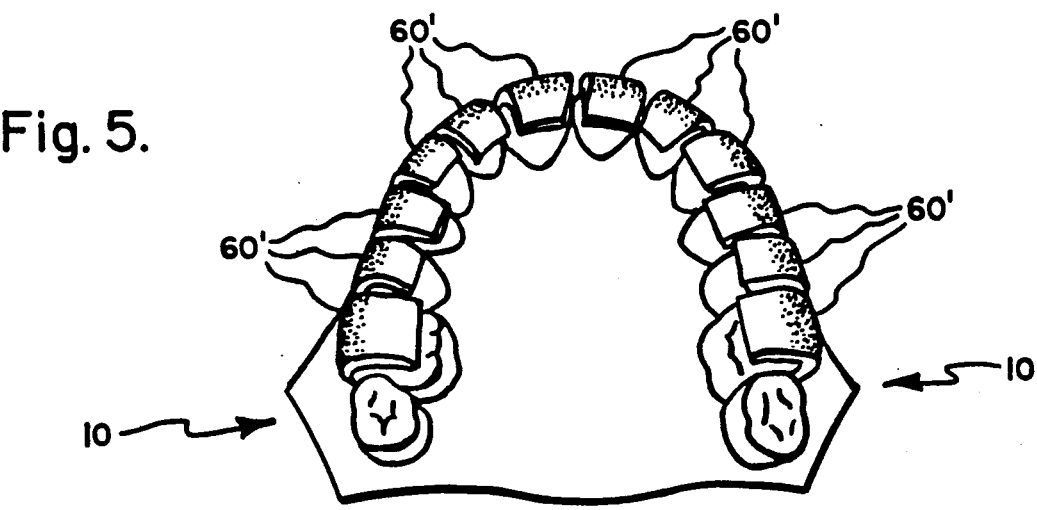
FIG. 5 is a top perspective view of the model of FIG. 4 and illustrating another stage in the method of forming the transfer matrix.

Referring to FIG. 4, the first step in the method of forming the transfer matrix according to the present invention is applying impression material 60 to construction model 26 with coupling members 40 thereon so as to locate the coupling members 40 relative to the respective teeth. One form of impression material found to perform satisfactorily is a silicone putty commercially available under the trade designation BondoSil from Ortho-Bonding Co., Delray Beach, Fla. The impression material is formed by hand on the dental arch of construction model 26, in the present illustration primarily on the facial surface of the teeth, so as to locate the positioning of the coupling members 40. Obviously if the coupling members were on the lingual surfaces of the teeth, the material would be formed primarily on the lingual surfaces. The impression material is allowed to cure, typically by simply standing for a period of time, whereupon it is separated such as by cutting into a plurality of segments, one for each tooth element. The segments then are transferred to and placed on the corresponding teeth elements of the original model 10 as shown in FIG. 5, these segments being designated 60'.

Figure 6:
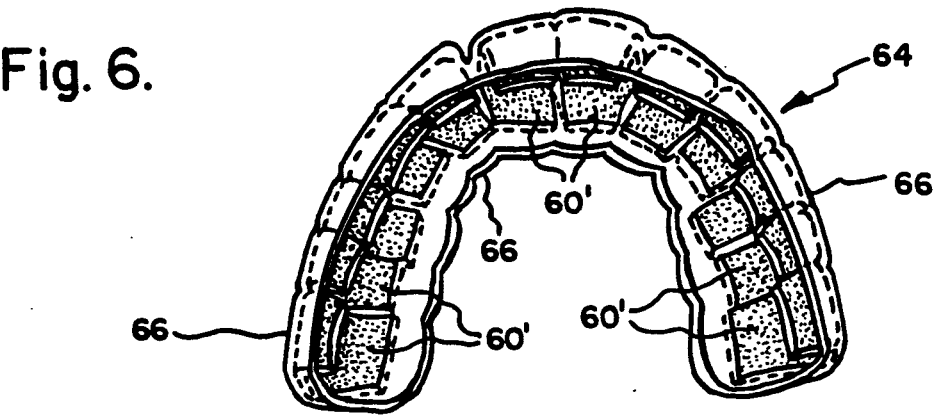
FIG. 6 is a top perspective view of a transfer matrix according to the present invention.
Figure 7:
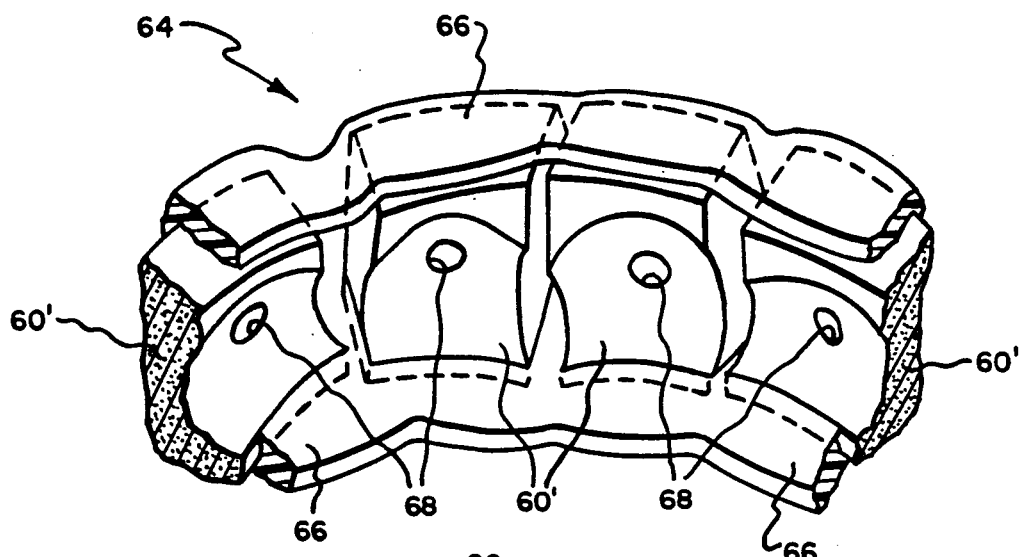
FIG. 7 is an enlarged fragmentary perspective view of the transfer matrix of FIG. 6.

The next step in forming the transfer matrix according to the present invention is forming a holder for capturing the segments by applying moldable material to the segments in a unitary body of the moldable material. A sheet of thermoplastic material is applied over the outer surfaces of the segments of impression material. The model 10 with impression material segments 60' and thermoplastic overlay can be placed in the afore-mentioned Biostar machine to form the thermoplastic material exactly to the outer shape of the segments and the dental arch. After shaping and when the thermoplastic material has cooled, the resulting assembly then is removed from model 10 and trimmed to form the resulting transfer matrix designated 64 in FIGS. 6 and 7. The body 66 of thermoplastic material serves as a carrier or holder for the segments 60' and maintains the relative position and location of the segments 60' as established by model 10. Model 10 is of course of the patient's actual dental arch and teeth in the actual position including some which are malaligned or maloccluded. Each segment has a recess 68 formed therein for receiving the coupling members. The transfer matrix can be divided into two or more parts if desired for ease in applying the coupling members to the patient's teeth which now will be described.

In use, coupling members are fitted into segments 60' in transfer matrix 64 with the entire coupling member snap-fitted into recess 68 with the bulbous end entering first and with the concave end face of each coupling member being substantially flush with the inner surface of each of the segments 60' and facing inwardly of the transfer matrix 64. Suitable adhesive is applied to the end face of each coupling member, for example Excel G9210D fast set adhesive commercially available from Great Lakes Orthodontics, Ltd. Then the transfer matrix is introduced to the patient's mouth and fitted onto the patient's dental arch, the surfaces of the segments 60' serving to guide the placement thereon. Each of the coupling members contacts a surface of a corresponding tooth of the patient and is located at the desired position on the tooth surface by virtue of the reference established by the transfer matrix. After the adhesive sets, the transfer matrix is removed and the coupling members remain attached to the patient's teeth. As a result, the patient's teeth are ready to receive the positioner of the present invention, for example the positioner 50 as shown and described in FIG. 3. In particular, the installation of the positioner 50 on the patient's actual teeth resembles that shown in FIG. 3 wherein positioner 50 is installed on the construction model with coupling members 40 attached to the teeth elements. Furthermore, the transfer matrix is used to attach coupling members to the patient's teeth for receiving other forms of the positioner of the present invention which now will be described.

Figure 8:
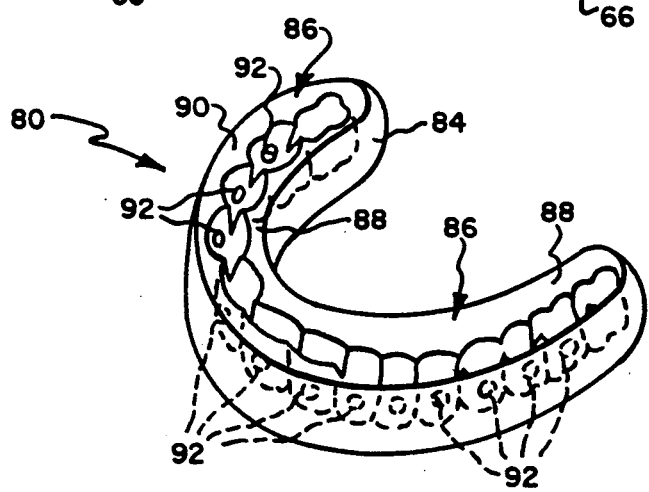
FIG. 8 is a perspective view of a half positioner according to another aspect of the present invention.
Figure 9:
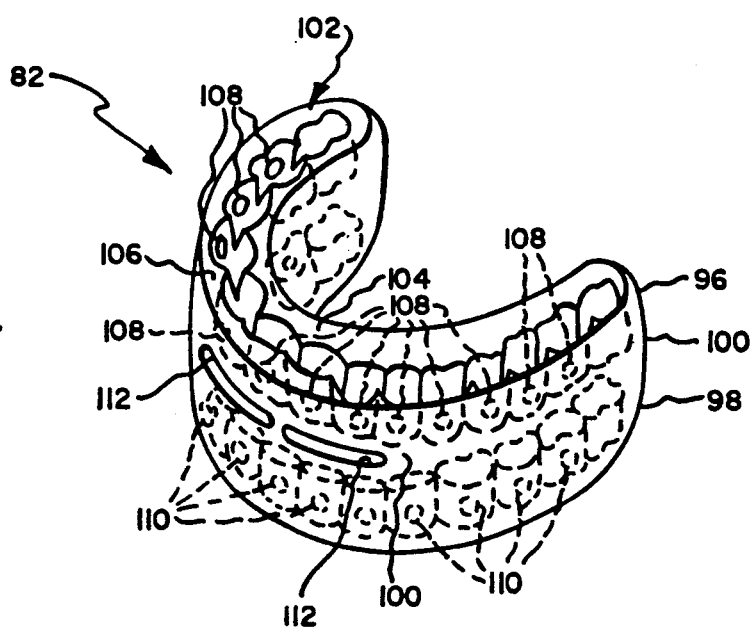
FIG. 9 is a perspective view of a full positioner according to another aspect of the present invention.

FIGS. 8 and 9 illustrate two forms of an orthodonitic positioner according to another embodiment of the present invention. The positioner of this embodiment is generally in the form of a commonly known mouthguard. Positioner 80 shown in FIG. 8 is for use on either dental arch of a patient, upper and/or lower, and positioner 82 shown in FIG. 9 is a full positioner which simultaneously receives the upper and lower dental arches of a patient. Both forms of positioner are of elastic material, in particular a silicone elastomer material, and are operatively positioned about the patient's teeth and in engagement with the coupling members attached to the patient's teeth, for urging particular ones of the patient's teeth toward a predetermined or desired position or orientation. Both positioners 80 and 82 are formed on construction models such as model 26 shown in FIG. 2 having coupling members 40 attached thereto.

Thus, positioner 80 comprises a body 84 of elastomer base material having an arcuate shape with a trough 86 for receiving teeth of the patient's dental arch. The trough 86 has walls 88,90 including surfaces adapted to contact the facial and lingual surfaces of the patient's teeth and the surfaces having recesses such as those designated 92 in spaced relation along the trough for fitting onto the coupling members attached to the patient's teeth. In the illustrative positioner of FIG. 8, recesses 92 are in surfaces along wall 90 for coupling to attachments on the facial surfaces of the patient's teeth. As previously pointed out, alternatively the recesses can be located for coupling to attachments on the lingual surfaces of the patient's teeth. When the positioner 80 is operatively positioned about the maloccluded or malaligned teeth of the patient, the body 84 is in a stretched or deformed condition and the elasticity of the body urges the patient's teeth toward the predetermined, desired orientation. In accordance with the present invention, the positioner 80 elastically urges the patient's teeth to an exact fit between the recesses 92 and the coupling members so as to eliminate any void or space between the coupling members and the recesses.

The full positioner 82 illustrated in FIG. 9 comprises a body of elastomer base material having an arcuate shape and including an upper portion 96 and a lower portion 98 separated by a mid portion 100. Each of the upper and lower portions 96 and 98 includes a trough conforming to the upper and lower dental arches, respectively, of the patient, the troughs facing in opposite directions. Thus, upper portion 96 includes a trough 102 having walls 104,106 adapted to contact the surfaces of the patient's teeth and the walls having recesses such as those designated 108 in spaced relation along the trough for fitting onto the coupling members attached to the patient's teeth along the upper dental arch. Similarly, a lower trough has walls adapted to contact the surfaces of the patient's teeth and the walls having recesses such as those designated 110 in spaced relation along the trough for fitting onto coupling members attached to the patient's teeth along the lower dental arch. Breathing passages or openings 112 can be provided in the front part of mid portion 100. In the illustrative positioner of FIG. 9, recesses 108 and 110 are for coupling to attachments on the facial surfaces of the patient's teeth. As previously pointed out, alternatively the recesses can be located for coupling to attachments on the lingual surfaces of the patient's teeth. When the positioner 82 is operatively positioned about the maloccluded or malaligned teeth of the patient, the body is in a stretched or deformed condition and the elasticity of the body urges the patient's teeth toward the predetermined, desired orientation. In accordance with the present invention, the positioner 82 elastically urges the patient's teeth to an exact fit between the recesses 108,110 and the coupling members attached to the patient's teeth so as to eliminate any space or void between the coupling members and the recesses.

One form of silicone elastomer material found to perform satisfactorily for positioners 80 and 82 is commercially available from Dow Corning under the designation SILASTIC Q7-4840. Other forms of low durometer, high elasticity elastomers can be employed.

The positioners 80 and 82 are formed preferably by injection molding in the following manner. Referring first to full positioner 82 shown in FIG. 9, a set of upper and lower construction models like lower model 26 of FIG. 2 with coupling members attached thereto, one model for the upper dental arch and the other model for the lower dental arch, are used as a base or standard upon which a wax pattern of the desired finishing positioner is formed. More specifically, the previously formed wax construction bite taken while the wax/stone models were operatively mounted within the articulator is operatively placed between the construction models and the construction models are operatively positioned upon the wax construction bite. The resulting arrangement between the construction models simulates the previously-obtained relationship between the wax/stone models mounted within the articulator. To secure the relationship between the construction models, peripheral edges of the wax construction bite are luted, or sealed with a heated instrument, to the construction models.

Additional wax is then applied to the inside and outside surfaces of the construction models in the form of heated wax sheets to complete the wax pattern for the resulting positioner 82. If desired, the peripheral design of the positioner can be penciled or outlined upon the construction models to provide a visual border for the build-up wax, and openings can be carved into the wax pattern to provide the breathing passages 112 in the resulting positioner 82.

Upon completion of the wax pattern, the construction models with the wax pattern positioned thereabout are used to mold the positioner 82. Such molding can be performed with investment molding equipment including an injection-type flask and carried out by molding techniques which are well known in the art. Briefly, the construction models and wax pattern are operatively positioned in the injection-type flask, and a plaster investment is poured around the models and pattern. The wax pattern is boiled out to define a mold cavity within the flask, and the wax pattern is replaced with uncured elastomer base material, such as the aforementioned SILASTIC Q7-4840 being injected into the mold cavity. After permitting the elastomer base material to cure to form the positioner 82, the positioner is removed from the investment and finished, as by trimming with scissors and/or smoothing with a coarse wheel mounted in a bench lathe chuck, to remove material flash from vents and sprue of the mold. The finished positioner 82 is then ready for insertion into the patient's mouth.

To facilitate the investment molding of the positioner 82, it has been found that when investing the flask with plaster, the flask be initially filled only to a height equal to about one-half the height of the wax pattern when positioned within the flask. The investment is then allowed to set, and a separator is spread thereover before the second half of the investment is poured. The resultant mold or casing formed upon filling the remaining one-half of the flask with investment comprises two mold halves. Furthermore, for purposes of permitting air to escape during the injection of the uncured elastomer base material, it is preferred that the mold cavity be vented by means of scored grooves to the edge of the investment. A trench is thereafter carved in the plaster to provide the main sprue through which elastomer is injected into the mold cavity. Still further, for purposes of preparing the mold cavity after boiling out the wax pattern, the mold halves are preferably dehydrated in a convection oven at about 150° Fahrenheit for about two hours. Before dehydration, a soap base separator is applied to the molds. After dehydration, the mold halves are secured and ready for injection.

With injection molding completed, the elastomer base material, and in particular SILASTIC Q7-4840, is cured by placing the filled mold within a heated, dry pressure vessel maintained at about 275° Fahrenheit at 15 p.s.i. and leaving the mold in the vessel for about one and one-half hours. The mold is then removed from the vessel and permitted to bench cool for about twenty minutes. The mold halves are then fractured to permit access to the molded positioner 82.

By way of background, a more detailed description of forming a full positioner by injection molding may be found in the above-identified application Ser. No. 046,087.

The split or half positioner 80 shown in FIG. 8 is formed in a substantially similar manner. Separate wax patterns are built upon each construction model to yield a pair of pattern-bearing construction models. Preferably, the wax patterns are indexed with one another to ensure proper fit-up of the resultant positioner parts within the mouth. Each construction model, with its corresponding wax pattern, is then used to investment mold a corresponding split positioner 80.

The positioners 50, 80 and 82 are used in a method of orthodontic treatment in the following manner. Coupling members are attached to the patient's teeth using transfer matrix 64 as previously described. Positioner 50 is installed on the patient's teeth during one portion of each day during the treatment period. That portion of the day is when the patient's teeth are most likely to be visible to others, typically daytime. Being in the form of a narrow band or strip, positioner 50 is less likely to be seen by others and is cosmetically more relatively pleasing to the eye. Thereafter, positioner 50 is removed and either positioner 80 or 82 is installed on the patient's teeth during the remaining portion of each day during the treatment period. That portion is when the patient's teeth are less likely to be visible to others, typically nightime.

The foregoing positioner system and procedure effectively results in substantially continuous application of forces to the patient's teeth in a manner acceptable to the patient in terms of comfort and appearance and with the resulting advantage of relatively shorter overall length of treatment time. The strip positioner 50 at the very least maintains the tooth movement previously applied by the positioner 80 and 82. Positioner 50 provides the secondary benefit of covering the coupling members between periods when positioners 80 and 82 is installed. The uncovered and exposed coupling members can be irritating to the tongue and other parts of the patient's mouth. The manner in which positioners 50, 80 and 82 are fabricated, in particular the positioner material being formed directly on the actual tooth attachments or coupling members during the fabrication process, assures accuracy of the appliance and compliance with the exact shape and placement of the attachment or coupling members. In particular, the positioner elastically urges the patient's teeth to an exact fit between the material of the positioner and the coupling members attached to the patient's teeth so as to eliminate any void or space therebetween thereby allowing a good purchase to the coupling members and therefore a good operative coupling to the patient's teeth. Transfer matrix 64 provides both simultaneous attachment of coupling members to the patient's teeth at the outset and individual attachment at a later time in the event that one or more coupling members become inadvertently detached from the patient's teeth.

It is therefore apparent that the present invention accomplishes its intended objects. While embodiments of the present invention have been described in detail, that is for the purpose of illustration, not limitation.

We claim:

1. A method of making an orthodontic elastic positioner for maloccluded or malaligned teeth located in a dental arch of a patient for coaction with teeth-mounted coupling members including portions protruding from the surfaces of the teeth including the steps of:
   a) providing a construction model of the patient's teeth and a portion of the gum tissue in the dental arch wherein the teeth therein are positioned in a desired orientation;
   b) attaching coupling members to the surfaces of the teeth in said construction model; and
   c) forming an elastic positioner by applying positioner material to said construction model and directly to said coupling members thereby providing an exact adaptation of said positioner material to said construction model including said coupling members and providing an exact fit between said positioner material and said coupling members so as to eliminate any void or space between said coupling members and said positioner material and to provide an accurate snap-on coupling and peel-off effect for said positioner with respect to the coupling members on the patient's teeth.

2. The method according to claim 1, wherein said step of the positioner is performed in a manner providing a positioner body in the form of an elongated strip having a length determined by the location of the coupling members and having a width initiating near the gingival line and terminating near the patient's dental arch to avoid interference in occlusion.

3. The method according to claim 2, wherein said step of forming the positioner is performed by a hand lay up technique and wherein said positioner material is a hand lay-up type of silicone elastomer material.

4. The method according to claim 2, further including the step of curing the resulting positioner.

5. The method according to claim 4, further including the step of removing the resulting positioner from said construction model.

6. The method according to claim 5, further including the step of trimming the resulting positioner.

7. The method according to claim 1, further including the step of forming a transfer matrix from said construction model with said coupling members attached thereon for use in attaching coupling members to the patient's teeth.

8. The method according to claim 7, wherein said step of forming a transfer matrix comprises:
   a) applying impression material to said construction model including said attachments so as to locate said coupling members relative to the respective teeth;
   b) separating said impression material into segments for each tooth;
   c) providing an original model of the patient's teeth and a portion of the gum tissue in the dental arch when the teeth therein are positioned in the actual and maloccluded orientation;
   d) transferring said segments from teeth of said construction model to corresponding teeth of said original model; and
   e) forming a holder for capturing said segments by applying moldable material to said segments in a unitary body of said moldable material.

9. The method according to claim 1 wherein said step of forming the positioner is performed by molding in a manner providing a positioner body having an arcuate shape including a trough for receiving teeth of the dental arch, the trough having walls including surfaces shaped exactly to the surfaces of the teeth of said construction model and including recesses shaped to said coupling members.

10. The method according to claim 9, wherein said step of molding comprises injection molding including the steps of:
   a) building a wax pattern of the desired positioner upon said construction model so as to provide a pattern-supporting construction model;
   b) providing investment molding equipment and an uncured amount of silicone elastomer base material from which said positioner is to be formed;
   c) operatively positioning the pattern-supporting construction model within the investment molding equipment and utilizing investment molding techniques to replace the wax pattern within the molding equipment with the uncured amount of silicone elastomer base material;
   d) permitting the amount of elastomer base material to cure to thereby provide the positioner; and
   e) removing the positioner from the investment molding equipment.

11. The method according to claim 1, wherein each of said coupling members is located on the surface of the respective so that the center of the coupling member is in substantial alignment with the center of rotation of the tooth.

12. A method of orthodontic treatment of maloccluded or malaligned teeth utilizing a positioner of elastic material in cooperation with teeth-mounted coupling members including portions protruding from the surfaces of the teeth including the
   a) providing a construction model of the patient's teeth and a portion of the gum tissue in the dental arch when the teeth therein are positioned in a desired orientation;
   b) attaching coupling members to the surfaces of the teeth in said construction model;
   c) forming a positioner by applying positioner material to said construction model and directly to said coupling members thereby providing an exact adaptation of said positioner material to said construction model including said coupling members and providing an exact fit between said positioner material and said coupling members so as to eliminate any void or space between said coupling members and said positioner material and to provide an accurate snap-on coupling and peel-off effect for said positioner with respect to the coupling members on the patient's teeth;

d) attaching coupling members to the surfaces of the patient's teeth in accordance with the locations of coupling members attached to the teeth of said construction model; and e) applying said positioner to the patient's teeth, said positioner elastically urging the patient's teeth to an exact fit between the material of said positioner and the coupling members attached to the patient's teeth so as to eliminate any void or space therebetween thereby allowing a good purchase to the coupling members and therefore a good operative coupling to the patient's teeth.

13. The method according to claim 12, wherein said step of forming the positioner is performed in a manner providing a positioner body in the form of an elongated strip having a length determined by the location of the coupling members and having a width initiating near the gingival line and terminating near the patient's opposing dental arch to avoid interference in occlusion.

14. The method according to claim 12, wherein said step of forming the positioner is performed by molding in a manner providing a positioner body having an arcuate recess including a trough for receiving teeth of the dental arch, the trough having walls including surfaces shaped exactly to the surfaces of the teeth of said construction model and including recesses shaped exactly to said coupling members.

15. The method according to claim 12, wherein said step of attaching coupling members to the surfaces of the patient's teeth is performed using a transfer matrix formed from said construction model with coupling members attached thereto.

16. A method of orthodontic treatment of maloccluded or malaligned teeth utilizing positioners of elastic material in cooperation with teeth-mounted coupling members including portions protruding from the surfaces of the teeth including the steps of:

a) attaching coupling members to the surfaces of the patient's teeth in a predetermined manner;

b) providing a first positioner having a body of elastic material in the form of an elongated strip having a length determined by the location of the coupling members and having a width initiating near the gingival line and terminating near the patient's opposing dental arch to avoid interference with occlusion, said strip having recesses in spaced relation therealong for fitting on said coupling members;

c) providing a second positioner having a body of elastic material in an arcuate shape including a trough for receiving teeth of the patient's dental arch, the trough having walls including surfaces shaped to the patient's teeth and including recesses shaped to said coupling members;

d) installing only the first positioner on the patient's period; and e) installing only the second positioner on the patient's teeth during another portion of a day during a treatment period.

17. A method according to claim 16, wherein said first positioner is installed on the patient's teeth during a portion of the day when the patient's mouth and teeth are most likely to be visible to others.

18. A method according to claim 16, wherein said second positioner is installed on the patient's teeth during a portion of the day when the patient's mouth and teeth are least likely to be visible to others.

19. A method according to claim 16, wherein said first and second positioners elastically urge the patient's teeth to an exact adaptation and fit to said coupling members so as to eliminate any void or space between said coupling members and said recesses of said positioners thereby allowing a good purchase to the coupling members and therefore a good operative coupling to the patient's teeth.

20. A method according to claim 16, wherein said coupling members are attached to the surfaces of the patient's teeth in a manner determined by the location of coupling members attached to a construction model of the patient's teeth in a desired orientation which is used in forming said positioners.

21. An orthodontic appliance for maloccluded or malaligned teeth to which are operatively secured coupling members of the type including portions protruding from the sides of the teeth, said appliance comprising:

a body of elastomer base material in the form of an elongated strip having a length determined by the location of the coupling members and having a width initiating near the gingival line and terminating near the patient's opposing dental arch to avoid interference in occlusion, said body having a surface facing the teeth and recesses in spaced relation along said strip for fitting onto said coupling members, said body elastically urging the patient's teeth to an exact fit between said recesses and said coupling members so as to eliminate any void or space between said coupling members and said recesses thereby allowing a good purchase to the coupling members and therefore a good operative coupling to the patient's teeth.

22. An orthodontic appliance according to claim 21, wherein said body is of silicone elastomer base material.

23. An orthodontic appliance according to claim 21, wherein said strip has a length determined by the number of teeth being positioned.

24. An orthodontic appliance according to claim 21, wherein each of said coupling members is formed to include an undercut.

25. An orthodontic appliance according to claim 21, wherein each of said coupling members is in the form of a mushroom-shaped button having a stem portion attached to the tooth surface and a bulbous portion protruding from the tooth surface.

26. An orthodontic appliance for maloccluded or malaligned teeth to which are operatively secured coupling members of the type including portions protruding from the surfaces of the teeth, said appliance comprising:

a body of elastomer base material having a arcuate shape including a trough for receiving teeth of the dental arch, the trough having walls including surfaces having recesses in spaced relation along said trough for fitting onto said coupling member, said body formed directly on the actual ones of said coupling members during fabrication of said body so that said body elastically urges the patient's teeth to an exact fit between said recesses and said coupling members so as to eliminate any void or space between said coupling members and said recesses thereby allowing a good purchase to the coupling members and therefore a good operative coupling to the patient's teeth.

27. An orthodontic appliance according to claim 26, wherein said body is of silicon elastomer base material.

28. An orthodontic appliance according to claim 26, wherein said body has a pair of troughs facing in opposite direction for receiving teeth of both the upper and lower dental arches.

29. An orthodontic appliance according to claim 26, wherein each of said coupling members is formed to include an undercut.

30. An orthodontic appliance according to claim 26, wherein each of said coupling members is in the form of a mushroom-shaped button having a stem portion attached to the tooth surface and a bulbous portion protruding from the tooth surface.

* * * * *

UNITED STATES PATENT AND TRADEMARK OFFICE
CERTIFICATE OF CORRECTION

PATENT NO. : 5,055,039

DATED : October 8, 1991

INVENTOR(S) : Gerard P. Abbatte, Peter R. Breads, Stephens P. Warunek and Brian D. Willison It is certified that error appears in the above-identified patent and that said Letters Patent is hereby corrected as shown below:

Column 13, line 2, (claim 2), change "Steps of the " to --Step of forming the--.

Column 13, line 6, (claim 2), change "patient dental" to --patient's opposing dental--.

Signed and Sealed this

Ninth Day of March, 1993

*Attest:*

STEPHEN G. KUNIN

*Attesting Officer*     Acting Commissioner of Patents and Trademarks